United States Patent [19]

Skuballa et al.

[11] 4,359,581

[45] Nov. 16, 1982

[54] PROCESS FOR THE PRODUCTION OF CARACYCLIN INTERMEDIATES

[75] Inventors: Werner Skuballa; Bernd Raduechel; Helmut Vorbrueggen, all of Berlin, Fed. Rep. of Germany

[73] Assignee: Schering AG, Berlin, Fed. Rep. of Germany

[21] Appl. No.: 270,716

[22] Filed: Jun. 5, 1981

[30] Foreign Application Priority Data

Jun. 6, 1980 [DE] Fed. Rep. of Germany ....... 3021895

[51] Int. Cl.$^3$ .................... C07D 309/12; C07D 37/20; C07C 69/757; C07C 69/76
[52] U.S. Cl. ...................................... 549/421; 560/53; 560/119; 556/436; 556/441; 549/475; 549/465; 542/426
[58] Field of Search ............................... 560/119, 53; 260/345.8 P, 347.4; 556/436, 441; 542/426; 549/465

[56] References Cited

FOREIGN PATENT DOCUMENTS 2017699 10/1979 United Kingdom ................ 560/119

OTHER PUBLICATIONS

Fieser and Fieser, Reagents for Organic Synthesis, vol. 1, pp. 306–307, John Wiley & Sons, Inc., New York, 1967.

*Primary Examiner*—Nicky Chan
*Attorney, Agent, or Firm*—Millen & White

[57] ABSTRACT

A process for preparing a 3-oxo-7-hydroxy-bicyclo[3,3,0]octan-2-ylcarboxylic acid ester of the formula

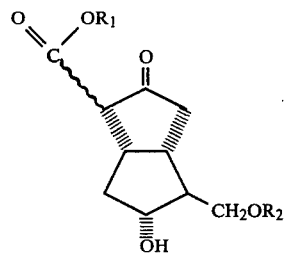

wherein
$R_1$ is alkyl of 1–6 carbon atoms or phenalkyl of 7–10 carbon atoms and
$R_2$ is hydrogen, alkyl or 1–6 carbon atoms, phenalkyl of 7–10 carbon atoms, tetrahydropyranyl, tetrahydrofuranyl, α-ethoxyethyl, tri-$C_{1-4}$-alkylsilyl, wherein the alkyl moieties can optionally be substituted by phenyl, or

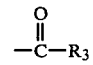

wherein $R_3$ is alkyl of 1–6 carbon atoms or aryl of 6–12 carbon atoms, comprises oxidizing the corresponding 7-hydroxy-2-oxabicyclo [3,3,0]octan-3-ylideneacetic acid ester of the formula

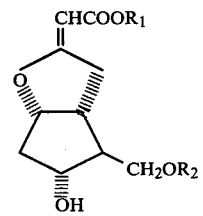

wherein
$R_1$ and $R_2$ are as defined above, to form the corresponding ketone, reacting the latter with a base which opens the ether oxygen containing ring, and then reducing the resultant product to prepare the 3-oxo-7-hydroxy-bicyclo[3,3,0]octan-2-ylcarboxylic acid ester.

9 Claims, No Drawings

PROCESS FOR THE PRODUCTION OF CARACYCLIN INTERMEDIATES

BACKGROUND OF THE INVENTION

The present invention relates to a process for the production of carbacycline intermediates from 7-hydroxy-2-oxabicyclo[3,3,0]octan-3-ylideneacetic acid esters. Advantage can be taken of this process to produce stable and pharmacologically active carbacycline derivatives.

DOS [German Unexamined Laid-Open Application] No. 2,912,409 describes a carbacyclin synthesis which starts with a bicyclic lactone and proceeds with an opening of the lactone ring, introduction of an acetic acid ester while forming a dicarboxylic acid ester with preceding hydrogenation, and finally, via cyclization, leads to the carbacycline intermediate. This synthesis not only involves considerable expenditure, but also entails marked losses in yield in its several stages, for example in the introduction of the methyl acetate residue into the open-ring lactone, but especially during the cyclizing of the dicarboxylic acid diester and the subsequent decarboxylation. Thus, there has been a need for an improved process.

SUMMARY OF THE INVENTION

It is an object of this invention to provide an improved process for preparing the mentioned carbacyclin intermediates.

Upon further study of the specification and appended claims, further objects and advantages of this invention will become apparent to those skilled in the art.

It has now been found that the prostacyclin precursor, 7-hydroxy-2-oxabicyclo[3,3,0]octan-3-ylideneacetic acid ester, can be reacted with bases after a preceding oxidation and a subsequent reduction, to the carbacycline intermediate 7-hydroxy-3-oxobicyclo[3,3,0]octan-2-ylcarboxylic acid ester in high yields.

Accordingly, in one aspect, these objects have been attained by this invention by providing a process for preparing 3-oxo-7-hydroxybicyclo[3,3,0]octan-2-ylcarboxylic acid esters of Formula I

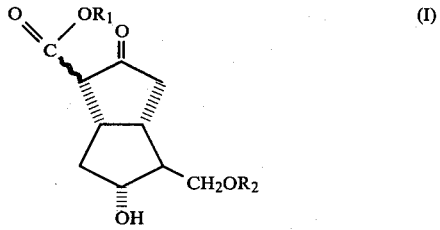 (I)

wherein $R_1$ is alkyl of 1–6 carbon atoms or aralkyl of 7–10 carbon atoms and $R_2$ is hydrogen, alkyl of 1–6 carbon atoms, aralkyl of 7–10 carbon atoms, tetrahydropyranyl, tetrahydrofuranyl, α-ethoxyethyl, trialkylsilyl, wherein each alkyl moiety is of 1–4 carbon atoms and can also be substituted by phenyl, or

wherein $R_3$ is alkyl of 1–6 carbon atoms or aryl, comprising reacting a 7-hydroxy-2-oxabicyclo[3,3,0]-octan-3-ylideneacetic acid ester of the formula II

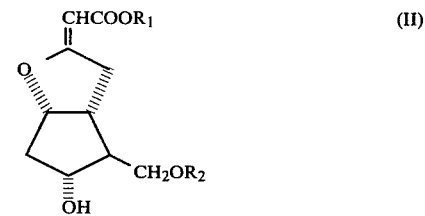 (II)

wherein $R_1$ and $R_2$ are as defined above, after preceding oxidation, in succession with bases and a reducing agent.

DETAILED DISCUSSION

Compounds of Formula I are excellent intermediates for the preparation of stable, pharmacologically active carbacyclin derivatives, e.g., prostacyclins, wherein the 9-ether oxygen is replaced by a methylene group. See, e.g., U.S. application Ser. No. 086,506 of Oct. 19, 1979, whose disclosure is incorporated by reference herein.

The first step of the process of this invention is an oxidation of the hydroxy group in the compounds of Formula II. This can be conducted according to conventional methods known to those skilled in the art. Examples of suitable oxidizing agents or oxidation methods include: Collins reagent (Tetrahedron Letters, 1968:3368), Jones reagent (J. Chem. Soc. 1953:2555), pyridinium chlorochromate (Tetrahedron Letters, 1975:2647), pyridinium dichromate (Tetrahedron Letters, 1979:399), or the Moffat-Pfitzner method (Fieser and Fieser, reagents for organic synthesis, Vol. 1, page 306–307, J. Wiley, N.Y.). All these disclosures are incorporated by reference herein. The oxidation can be carried out under conventional conditions, e.g., with Collins reagent at −20° to +30° C., preferably 0°–5° C.; with Jones reagent at −40° to +30° C., preferably −30° to 0° C.; with pyridinium chlorochromate or pyridinium dichromate at −20° to +40° C., preferably at 20°–30° C., in a solvent inert with respect to the oxidation agent. Depending on the reagent employed, suitable solvents include methylene chloride, chloroform, ethylene chloride, dimethylformamide, pyridine, and others. The ketone wherein $R_1$ and $R_2$ are as defined above, is obtained in a practically quantitative yield and can be further reacted without any additional purification.

Suitable bases for use in the subsequent step include: Bicyclic tertiary amines, such as 1,5-diazabicyclo[4,3,0]-non-5-ene (DBN) and 1,8-diazabicyclo[5,4,0]undec-7-ene (DBU), potassium tert-butylate, sodium tert-butylate and similar alkali alcoholates.

Especially preferred bases are DBN and DBU. The reaction can proceed with or without the addition of a solvent at −40° to +60° C., usually for 0.2–24 hours, preferably at 0°–30° C. Suitable solvents include: tetrahydrofuran, diethyl ether, dioxane, toluene, etc. Generally, the amount of base added is in excess (>1 equivalent) based on the ketone, i.e., an amount effective to open the ether-containing ring.

The subsequent reduction of the keto group can be conducted in the same reactor by adding customary reducing agents under conventional conditions, e.g., at temperatures of −80° to +30° C., preferably −30° to +10° C. Suitable reducing agents include, for example, sodium borohydride, lithium tri-tert-butoxyaluminum hydride, zinc borohydride, aluminum isopropylate, etc., preferably sodium borohydride. To improve solubility, an alcohol can suitably be added, e.g., methanol, ethanol, propanol, isopropanol and the like.

Although a thin-layer chromatographic analysis of the crude product of the compounds of Formula I shows only minor amounts of accompanying substances, and accordingly, a purification is actually not indicated, a chromatographic purification step can be carried out, if desired. In the process of this invention, the pure compounds of Formula I are obtained from the compounds of Formula II in a total yield of about 70% of theory.

Saturated alkyl residues of 1-6 carbon atoms include straight-chain or branched alkyl residues, such as, for example, methyl, ethyl, n-propyl, isopropyl, n-butyl, isobutyl, sec-butyl, tert-butyl, n-pentyl, isopentyl, tert-pentyl, neopentyl, n-hexyl, isohexyl, etc. Especially preferred are alkyl residues of 1-4 carbon atoms.

Suitable aralkyl residues of 7-10 carbon atoms include phenylalkyl residues wherein the alkyl group can be branched, e.g., phenylmethyl, phenethyl, α-phenylethyl, phenylpropyl, phenylbutyl, α-phenylpropyl, α-phenylbutyl, etc. Phenylalkyl residues of 7-8 carbon atoms are preferred.

The alkyl residues of the trialkylsilyl group in $R_2$ can be straight-chain or branched and can also be substituted by phenyl (for example, 2-phenylbutyl, 3-phenylpropyl, phenylmethyl, etc.), e.g., methyl, ethyl, n-propyl, isopropyl, n-butyl, isobutyl, sec-butyl, tert-butyl, etc. The alkyl groups need not be the same.

Aryl groups for $R_3$ can have 6-12 carbon atoms, e.g., phenyl, α- and β-naphthyl, biphenylyl, and phenyl substituted by chlorine, bromine, $C_{1-4}$-alkyl or $C_{1-4}$-alkoxy. Suitable such alkyl residues of 1-4 carbon atoms include methyl, ethyl, n-propyl, isopropyl, n-butyl, isobutyl, sec-butyl, tert-butyl, etc. Suitable such alkoxy residues of 1-4 carbon atoms include methoxy, ethoxy, n-propoxy, isopropoxy, n-butoxy, isobutoxy, tert-butoxy, etc.

The starting material of Formula II required for the process of this invention can be conventionally produced from corresponding conventional lactones of Formula III

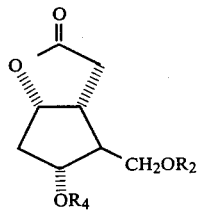
(III)

wherein
$R_2$ is as defined above, and
$R_4$ is hydrogen or

wherein $R_3$ is as defined above, by reaction with a lithium acetic acid ester of Formula IV

(IV)

wherein
$R_1$ is as defined above, in a solvent suitable for organometallic reactions, at temperatures of −80° to 0° C., preferably −70° to −50° C.

Suitable solvents include diethyl ether, tetrahydrofuran, dioxane, dimethoxyethane, etc. To split off water, the crude product of the organometallic reaction is treated with a catalytic amount of an acid in a solvent which is not miscible with water, e.g., toluene, methylene chloride, chloroform, carbon tetrachloride, diethyl ether, etc., preferably toluene, at a temperature of 20° to 100° C., preferably 20°-30° C. Examples of suitable acids include p-toluenesulfonic acid, sulfuric acid, hydrochloric acid, boron trifluoride, etc.

The saponification of the optionally present acyl groups can be effected, e.g., with alkali metal carbonates or alkaline earth metal carbonates in an alcohol. Suitable alcohols include aliphatic alcohols, e.g., methanol, ethanol, butanol, etc., preferably methanol. Examples of suitable alkali carbonates or alkaline earth carbonates include potassium carbonate, sodium carbonate, calcium carbonate, barium carbonate, etc. The reaction takes place at −10° to 70° C., preferably at 25° C.

The further conversion of the compounds of Formula I into carbacyclin derivatives is effected according to any conventional modus operandi, for example by decarbalkoxylation with, for example, 1,4-diazabicyclo[2,2,2]octane in toluene, esterification with, for example, benzoyl chloride or acetic anhydride, and splitting off of the blocking group. The thus-obtained ketone of Formula V

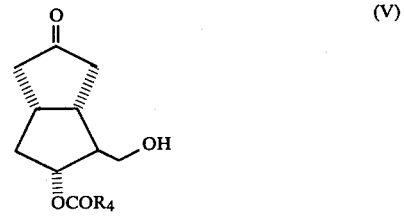
(V)

wherein
$R_4$ is as defined above, can be converted into the desired carbacyclin, for example, by following the procedures disclosed in DOS No. 2,912,409 or DOS No. 2,845,770.

The alcohol XIX is esterified to the ester XX with benzoyl chloride in the presence of pyridine:

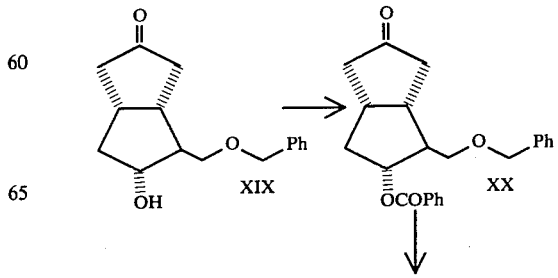

-continued

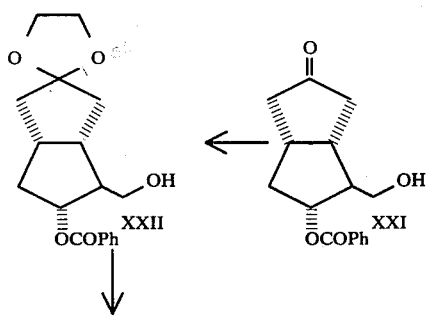

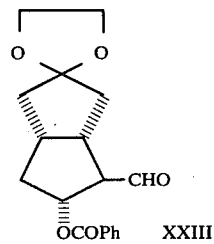

(Ph is phenyl)

Splitting of the benzyl ether by hydrogenolysis in the presence of catalytic amounts of an acid yields the alcohol XXI which is oxidized, after ketalization to the compound XXII, with Collins reagent to obtain the aldehyde XXIII.

This aldehyde is reacted with a phosphonate of Formula XXIV

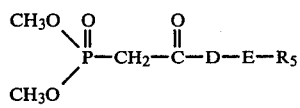

wherein D, E and $R_5$ are as defined below, in an olefin-forming reaction to a ketone of Formula XXV

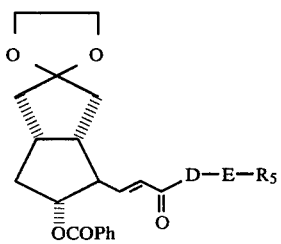

After reduction of the 15-keto group with zinc borohydride or sodium borohydride or reaction with alkyl magnesium bromide or alkyl lithium and separation of epimers, the 15α-alcohols XXVI are obtained (PG numbering):

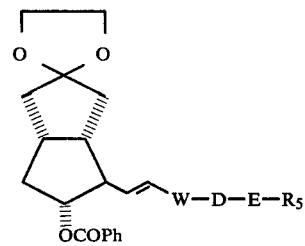

After saponification of the ester group, for example, with potassium carbonate in methanol, and splitting the ketal with aqueous acetic acid, the ketone of Formula XXVII is obtained:

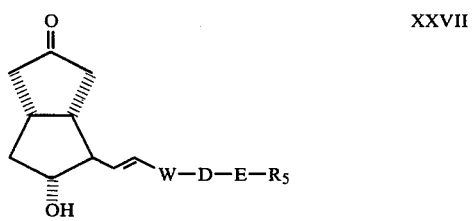

which, optionally after functional modification of the free hydroxy groups, for example, by etherification with dihydropyran or optionally hydrogenation of the double bond, is converted into the compounds of Formula VI:

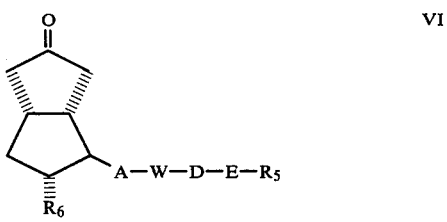

wherein $R_5$, $R_6$, A, W, D and E are as defined below.

Compounds of Formula VI can be used to prepare prostane derivatives of Formula VII 1. A prostane derivative of the formula

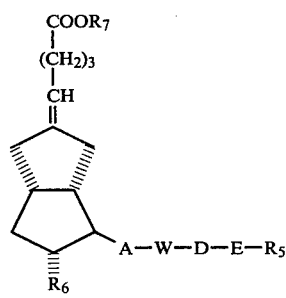

wherein $R_7$ is (a) hydrogen, (b) $C_{1-10}$ alkyl, (c) $C_{1-10}$ alkyl substituted by halogen; $C_{1-4}$ alkoxy; $C_{6-10}$ aryl; $C_{6-10}$ aryl substituted by 1–3 halogen atoms, a phenyl group, 1–3 $C_{1-4}$ alkyl groups or a chloromethyl, fluoromethyl, trifluoromethyl, carboxy, hydroxy or $C_{1-4}$ alkoxy group; di-$C_{1-4}$-alkylamino; or tri-$C_{1-4}$-alkylammonium; (d) $C_{4-10}$ cycloalkyl, (e) $C_{4-10}$ cycloalkyl substituted by $C_{1-4}$ alkyl, (f) $C_{6-10}$ aryl, (g) $C_{6-10}$ aryl substituted by 1–3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group, or (h) an aromatic heterocycle of 5 or 6 ring atoms one of which is O, N or S;

A is —$CH_2$—$CH_2$—, trans—CH=CH or C≡C;

W is hydroxymethylene, RO-methylene,

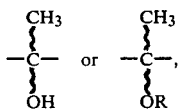

wherein OH or OR is in the α- and/or β-position and

R is an in vivo hydrolyzable and physiologically acceptable ether or acyl group which is conventional for modifying OH groups in prostaglandins;

D and E together are a direct bond, or

D is $C_{1-10}$ alkylene, $C_{1-10}$ alkenylene or $C_{1-10}$ alkynylene or one of these groups substituted by fluorine, and E is oxygen, —C≡C— or a direct bond;

$R_5$ is (a) a $C_{1-10}$ hydrocarbon aliphatic radical, (b) a $C_{6-10}$ hydrocarbon aliphatic radical substituted by $C_{6-10}$ aryl or by $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; (c) $C_{4-10}$ cycloalkyl, (d) $C_{4-10}$ cycloalkyl substituted by $C_{1-4}$ alkyl, (e) $C_{6-10}$ aryl, (f) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; or (h) an aromatic heterocycle of 5 or 6 ring atoms one of which is O, N or S; and $R_6$ is OH or OR; and, when $R_7$ is hydrogen, the salts thereof with physiologically compatible bases.

A process for the preparation of prostane derivatives of Formula VII, comprises in a conventional manner, reacting a compound of Formula VI optionally after blocking any free hydroxy groups therein, with a Wittig reagent of Formula VIII

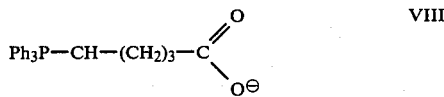

wherein Ph is phenyl. The reaction can be conducted conventionally unless otherwise indicated herein, e.g., as described in J. S. Bindra Prostaglandin Synthesis, page 210, Academic Press N.Y., 1977 whose disclosure is incorporated by reference herein. Optionally, thereafter, in any desired sequence, any isomers can be separated, and/or blocked hydroxy groups can be liberated, and/or free hydroxy groups can be esterified or etherified, and/or free carboxy groups can be esterified, and/or esterified carboxy groups can be saponified and/or carboxy groups can be converted into a salt with a physiologically compatible base.

The reaction of a compound of Formula VI with a Wittig reagent of Formula VIII, which can be produced by reacting the corresponding phosphonium salt with methanesulfinylmethyl sodium or methanesulfinylmethyl potassium or potassium tert-butylate in dimethyl sulfoxide, can be conducted at temperatures of 0°–100° C., preferably 20°–80° C., in an aprotic solvent, preferably dimethyl sulfoxide or dimethylformamide. The separation of the thus-obtained olefins of a Z- and E-configuration is conducted using fully conventional methods, for example, by column or layer chromatography.

The saponification of the prostaglandin esters is effected by following fully conventional methods known to those skilled in the art, for example, using alkaline catalysts. Similarly, the introduction of the ester group in the compounds wherein $R_7$ is $C_{1-10}$ alkyl is accomplished according to conventional methods known to persons skilled in the art. For example, the carboxy compounds can be reacted with diazo hydrocarbons in a conventional manner, for example, by mixing a solution of the diazo hydrocarbon in an inert solvent, preferably in diethyl ether, with the carboxy compound in the same or in another inert solvent, e.g., methylene chloride. After the reaction is terminated in 1-30 minutes, the solvent is removed and the ester is purified in conventional fashion. Diazoalkanes are either known or can be produced according to conventional methods [See, e.g., Org. Reactions, 8:389-394 (1954), whose disclosure is incorporated by reference herein].

The introduction of the ester group in the compounds wherein $R_7$ is a substituted or unsubstituted aryl group, can also be conducted according to methods known to persons skilled in the art. For example, the carboxy compounds can be reacted with the corresponding arylhydroxy compounds using dicyclohexylcarbodiimide in the presence of a suitable base, for example, pyridine or triethylamine, in an inert solvent. Suitable solvents include methylene chloride, ethylene chloride, chloroform, ethyl acetate, tetrahydrofuran, etc., preferably chloroform. The reaction is carried out at temperatures of −30° C. to +50° C., preferably about +10° C.

The prostaglandin derivatives of Formula VII wherein $R_7$ is hydrogen can be conventionally converted into salts using suitable amounts of the corresponding inorganic bases under normal neutralization conditions. For example, when dissolving the corresponding PG acids in water containing a stoichiometric quantity of the base, the solid inorganic salt can be obtained after evaporation of the water or after the addition of a water-miscible solvent, for example, alcohol or acetone.

To produce an amine salt, which is also done in the conventional manner, the PG acid is dissolved, for example, in a suitable solvent, e.g., ethanol, acetone, diethyl ether or benzene, and at least a stoichiometric amount of the amine is added to this solution. During this process, the salt is ordinarily obtained in the solid form or is isolated in conventional fashion after evaporation of the solvent.

The functional modification of the free OH-groups also takes place according to conventional methods known to those skilled in the art. To introduce the ether blocking groups, the reaction can be conducted, for example, with dihydropyran in methylene chloride or chloroform with the use of an acidic condensation agent, e.g., p-toluenesulfonic acid. The dihydropyran is utilized in excess, preferably twice to ten times the amount of the theoretical requirement. The reaction is normally terminated at 0° C.-30° C. after 15-30 minutes.

The acyl blocking groups are introduced by reacting a compound of Formula VII in a conventional manner with a carboxylic acid derivative, e.g., an acid chloride, acid anhydride, etc.

The liberation of a functionally modified OH-group to obtain the free OH-containing compounds of Formula VII similarly takes place according to conventional methods. For example, ether blocking groups can be split off in an aqueous solution of an organic acid, e.g., acetic acid, propionic acid, etc., or in an aqueous solution of an inorganic acid, e.g., hydrochloric acid. To improve solubility, a water-miscible, inert organic solvent can be suitably added. Suitable organic solvents include, for example, alcohols, such as methanol and ethanol, and ethers, such as dimethoxyethane, dioxane, and tetrahydrofuran. Tetrahydrofuran is preferably employed. The splitting-off step is conducted preferably at temperatures of 20° C.–80° C.

The splitting-off of the silyl ether blocking groups can be effected, for example, with tetrabutylammonium fluoride. Examples of suitable solvents include tetrahydrofuran, diethyl ether, dioxane, methylene chloride, etc. The splitting-off step is preferably conducted at temperatures of 0° C.–80° C.

The saponification of the acyl groups can be conducted, for example, using alkali metal or alkaline earth carbonates or hydroxides in an alcohol or in an aqueous solution of an alcohol. Suitable alcohols include aliphatic alcohols, e.g, methanol, ethanol, butanol, etc., preferably methanol. Suitable alkali metal carbonates and hydroxides include those of potassium and sodium, the potassium salts being preferred. Examples of suitable alkaline earth carbonates and hydroxides include calcium carbonate, calcium hydroxide, and barium carbonate. The reaction generally takes place at −10° to +70° C., preferably at about 25° C.

The compounds of Formula VII have a blood pressure lowering effect and a bronchodilatory activity. They are furthermore suitable for inhibiting thrombocyte aggregation. Consequently, the novel prostacyclin derivatives of Formula VII are valuable pharmacological agents. Moreover, they exhibit, with a similar spectrum of effectiveness, a higher specificity as compared to corresponding prostaglandins, and, above all, a substantially longer efficacy. As compared to $PGI_2$, they are distinguished by a higher stability. The high tissue specificity of the novel prostaglandins can be established by a conventional test on smooth-muscle organs, such as, for example, the guinea pig ileum or the isolated rabbit trachea, where a substantially lower stimulation can be observed than for the application of natural prostaglandins of the E-, A, or P-type. The novel prostaglandin analogs possess properties typical of prostacyclins, such as, for example, lowering of the peripheral arterial and coronary vascular resistance, inhibition of thrombocyte aggregation and lysis of platelets clots, myocardial cytoprotection and thus a lowering of the systemic blood pressure without lowering at the same time the cardiac output and coronary blood perfusion and stroke, prophylaxis and therapy of coronary heart disease, coronary thrombosis, myocardial infarction, peripheral arterial disease, arteriosclerosis, thrombosis, therapy of shock, inhibition of bronchoconstriction, inhibition of gastric acid secretion and cytoprotection of the gastric and intestinal mucosa, antiallergic properties, lowering of pulmonary vascular resistance and of pulmonary blood pressure, promotion of kidney blood flow, application instead of heparin or as adjuvans in dialysis of haemo-filtration, conservation of blood plasma, especially of blood platelets, inhibition of labour-pains, treatment of gestosis, increase of cerebral blood flow, etc. Additionally, the novel prostaglandin analogs display antiproliferative properties.

Upon intravenous injection into nonanesthetized, hypertonic rats in doses of 5, 20, and 100 μg/kg of body weight, the compounds of this invention display a stronger blood pressure lowering effect, and of a longer duration, than $PGE_2$ and $PGA_2$ compounds, without triggering diarrhea as do the $PGE_2$ compounds or cardiac arrythmias as do the $PGA_2$ compounds.

Upon intravenous injection into narcotized rabbits, the compounds of this invention, as compared to $PGE_2$ and $PGA_2$ compounds, display a stronger blood pressure lowering effect of a considerably longer duration, without affecting other smooth-muscle organs or organ functions.

The pharmacologically active compounds of this invention can be processed in accordance with conventional methods of galenic pharmacy to produce medicinal agents, especially for oral administration. Conventional excipients are pharmaceutically acceptable organic or inorganic carrier substances suitable for parenteral, enteral or topical application which do not deleteriously react with the active compounds. Suitable pharmacologically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 0.01–100 mg in a pharmaceutically acceptable carrier per unit dosage.

The dosage of the compounds according to this invention is 1–1500 μg/kg/day when administered to human patients as drugs for the treatment of the mentioned diseases.

Thus, e.g., sterile, injectable, aqueous or oily solutions are utilized for parenteral administration. Suitable for oral application are, for example, tablets, dragees or capsules.

The invention thus also relates to medicinal agents comprising the compounds of this invention and customary excipients and vehicles.

The active agents of this invention can serve, in conjunction with the auxiliary agents known and customary in galenic pharmacy, for example, for the production of blood pressure lowering agents.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1A

Ethyl Ester of [(1S,2RS,5S,6S,7R)-7-Hydroxy-3-oxo-6-(dimethyl-tert.-butylsilyloxymethyl)bicyclo[3,3,0]octan-2-yl]carboxylic Acid At ice bath temperature, a solution of 94.4 g of the ethyl ester of (1S,5R,6S,7R)-7-hydroxy-6-(dimethyl-tert.-butylsilyloxymethyl)-2-oxabicyclo[3,3,0]octan-3-ylideneacetic acid in 1.6 l of methylene chloride is added to a solution of 540 g of Collins reagent in 4.6 l of methylene chloride (absolute), and the mixture is agitated for 15 minutes at 5° C. The mixture is then diluted with 10 l of ether, the organic phase is stirred four times with 5% sodium bicarbonate solution, once with water, twice with 10% sulfuric acid, and three times with water, dried over sodium sulfate, and evaporated under vacuum.

The ketone (95 g) obtained in this way is dissolved in 320 ml of tetrahydrofuran, combined at 0° C. with 134 ml of 1,5-diazabicyclo[4,3,0]non-5-ene, stirred for 105 minutes at 0° C., cooled to −20° C., and 10.2 g of sodium borohydride and thereafter 385 ml of methanol are added to the reaction mixture. The latter is agitated for 100 minutes at −20° C., combined with 160 ml of acetone, stirred for 30 minutes, and then poured on 2 l of 10% citric acid solution. The reaction mixture is extracted with ether, the organic phase is washed neutral with water, dried over sodium sulfate, and evaporated under vacuum. Chromatography of the residue on silica gel yields, with hexane/ether (3+2), 65.5 g of the title compound as a colorless oil.

IR (CHCl$_3$): 3520, 2955, 2930, 2860, 1750, 1720, 1660, 1620, 834 cm$^{-1}$

The starting material for the above title compound is prepared as follows:

1A(a); (1S,5R,6S,7R)-7-Benzoyloxy-6-(dimethyl-tert.-butyl-silyloxymethyl)-2-oxabicyclo[3,3,0]octan-3-one At 0° C., 65 g of tert.-butyldimethylsilyl chloride is added to a solution of 100 g of (1S,5R,6S,7R)-7-benzoyloxy-6-hydroxymethyl-2-oxabicyclo[3,3,0]octan-3-one and 62 g of imidazole in 110 ml of dimethylformamide, and the mixture is stirred under argon for 24 hours at 24° C. Subsequently, the mixture is diluted with 6 l of ether, shaken twice with 5% sulfuric acid, four times with water, dried over magnesium sulfate, and evaporated under vacuum. The residue is recrystallized from hexane/methylene chloride, thus obtaining 137 g of the silyl ether as colorless crystals (mp 75° C.).

1A(b) Ethyl Ester of (1S,5R,6S,7R)-7-Hydroxy-6-(dimethyl-tert.-butyl-silyloxymethyl)-2-oxabicyclo[3,3,0]octan-3-ylideneacetic Acid Under argon 425 ml of a 1.6-molar butyllithium solution in hexane is added dropwise at −25° C. to 95 ml of diisopropylamine; the mixture is agitated for 1 hour at −25° C. At −70° C., 66 ml of ethyl acetate is added dropwise to this mixture, and the latter is stirred for 20 minutes, whereafter a solution of 66 g of the silyl ether obtained according to Example 1A(a); in 500 ml of diethyl ether and 500 ml of tetrahydrofuran is added thereto. The mixture is agitated for 20 minutes at −70° C., then poured on a mixture of 1.4 l of saturated ammonium chloride solution and 1.4 l of 10% citric acid solution, extracted with ether, and the organic extract is washed neutral with water, dried over magnesium sulfate, and evaporated under vacuum. The residue is dissolved in 1.5 l of toluene, and 1.5 g of p-toluenesulfonic acid is added thereto. The mixture is stirred for 2 hours at 25° C. and then evaporated under vacuum at 40° C. The mixture is then combined with 24 g of potassium carbonate (anhydrous), 500 ml of methanol is added thereto, and the mixture is stirred for 3 hours at 25° C. under argon, then diluted with ether, washed neutral with brine, dried with sodium sulfate, and evaporated under vacuum. Chromatography of the residue on silica gel yields, with hexane/ethyl acetate (7+3), 48 g of the title compound as colorless crystals (mp 35° C.).

IR (CHCl$_3$): 3520, 2955, 2930, 2860, 1742, 1635, 832 cm$^{-1}$

EXAMPLE 2A

Ethyl Ester of [(1S,2RS,5S,6S,7R)-6-Benzyloxymethyl-7-hydroxy-3-oxabicyclo[3,3,0]octan-2-yl]carboxylic Acid At ice bath temperature, a solution of 5 g of (1S,5R,6S,7R)-6-benzyloxymethyl-7-hydroxy-2-oxabicyclo[3,3,0]octan-3-ylideneacetic acid ethyl ester [Example 2A(a)] in 90 ml of methylene chloride is added to a solution of 30 g of Collins reagent in 250 ml of methylene chloride; the mixture is agitated for 15 minutes at 5° C., then diluted with 600 ml of ether, shaken four times with 5% sodium bicarbonate solution, once with water, twice with 10% sulfuric acid, and three times with water, then dried over magnesium sulfate, and evaporated under vacuum.

The residue (5 g) is dissolved in 18 ml of tetrahydrofuran, combined at 0° C. with 7.5 ml of 1,5-diazabicyclo[4,3,0]non-5-ene, agitated for 100 minutes at 0° C., cooled to −20° C., and then 550 mg of sodium borohydride and 18 ml of methanol are added. The reaction mixture is stirred for 100 minutes at −20° C., combined with 10 ml of acetone, agitated for 30 minutes, and then poured on 100 ml of 10% citric acid solution. The mixture is extracted with ether, the organic phase washed neutral with water, dried over magnesium sulfate, and evaporated under vacuum. Chromatography of the residue on silica gel yields, with ether/hexane (3+2), 3.4 g of the title compound as a colorless oil.

IR (CHCl$_3$): 3540, 2930, 2860, 1755, 1725, 1660, 1620 cm$^{-1}$

The starting material for the above title compound is prepared as follows:

2A(a) Ethyl Ester of (1S,5R,6S,7R)-6-Benzyloxymethyl-7-hydroxy-2-oxabicyclo[3,3,0]octan-3-ylideneacetic Acid At −25° C., 550 ml of a 0.91-molar butyllithium solution in hexane is added dropwise under argon to 69 ml of diisopropylamine and the mixture is agitated for 1 hour at −25° C. At −70° C., 49 ml of ethyl acetate is added dropwise to this mixture, and the latter is agitated at −70° C. for 20 minutes. Then a solution of 26.2 g of (1S,5R,6S,7R)-6-benzyloxymethyl-7-hydroxy-2-oxabicyclo[3,3,0]octan-3-one in 300 ml of diethyl ether and 300 ml of tetrahydrofuran is added thereto. After 20 minutes, the reaction mixture is poured on 1 l of saturated ammonium chloride solution, extracted with ether, the organic extract washed neutral with brine, and dried over magnesium sulfate.

The evaporation residue is dissolved in 700 ml of toluene, 0.25 g of p-toluenesulfonic acid is added, the mixture is stirred for 2 hours at 25° C., distilled under vacuum at 40° C. to remove about 400 ml of toluene, washed neutral with water, dried over magnesium sulfate, and evaporated under vacuum. Chromatography of the residue on silica gel yields, with hexane/ethyl acetate, 20.3 g of the title compound as colorless crystals (mp 59° C. from pentane/ether).

IR (CHCl$_3$): 3540, 2990, 2945, 1695, 1639, 1120 cm$^{-1}$

EXAMPLE 3A (1R,5S,6S,7R)-7-Benzoyloxy-6-hydroxymethylbicyclo[3,3,0]octan-3-one A solution of 47 g of the β-keto ester produced according to Example 1 in 1.2 l of toluene is combined with 157 g of 1,4-diazabicyclo[2,2,0]octane, and the mixture is refluxed under argon for 5 hours. Then the mixture is concentrated under vacuum, the residue is taken up in 320 ml of tetrahydrofuran, combined at 0° C. with 23 ml of benzoyl chloride, and agitated for 15 minutes at 0° C. The mixture is combined with 9 ml of water, agitated for 2 hours at 25° C., the crystalline slurry is dissolved in 2.5 l of ether, shaken repeatedly with 10% sulfuric acid and twice with water, and evaporated under vacuum. The residue is stirred for 5 hours at 30° C. in a mixture of glacial acetic acid, water, tetrahydrofuran (65+35+10), and then evaporated under vacuum. After chromatography of the residue on silica gel, 24.2 g of the title compound is obtained with ether in the form of a colorless oil.

IR (CHCl$_3$): 3510, 2945, 1739, 1712, 1602, 1588, 1278 cm$^{-1}$

REFERENCE EXAMPLES

1(n)

(1R,5S,6S,7R)-7-Benzoyloxy-6-benzyloxymethylbicyclo[3,3,0]octan-e-one

A solution of 0.55 g. of the alcohol of formula XIX in 4 ml. of pyridine is combined with 0.5 ml of benzoyl chloride. The mixture is agitated for 4 hours at 25°, combined with 0.4 ml of water agitated for 2 hours, diluted with ether, and the mixture is shaken in succession with water, 5% sulfuric acid, water, 4% sodium bicarbonate solution, and three times with water. After drying over magnesium sulfate the mixture is evaporated under vacuum, thus obtaining 720 mg. of the benzoate as a colorless oil.

IR: 2945, 2860, 1739, 1713, 1602, 1588, 1276 cm$^{-1}$.

1(o)

(1R,5S,6S,7R)-7-Benzoyloxy-6-hydroxymethylbicyclo[3,3,0]octan-3-one

A solution of 680 mg. of the benzoate prepared according to Reference Example 1(n) in 10 ml. of ethyl acetate and 0.5 ml. of glacial acetic acid is combined with 120 mg. of palladium on charcoal (10%) and shaken for 8 hours under a hydrogen atmosphere. Filtration and evaporation of the solution under vacuum yields 600 mg. of an oily crude product, which is purified by chromatography on silica gel with pentane/ethyl acetate (1+1), and 395 mg. of the pure alcohol as a colorless oil.

IR: 3500, 2945, 1739, 1712, 1602, 1588, 1278 cm$^{-1}$.

1(p)

(1R,5S,6S,7R)-3,3-Ethylenedioxy-7-benzoyloxy-6-hydroxymethylbicyclo[3,3,0]octane 320 mg. of the alcohol prepared according to Reference Example 1(o), 0.5 ml. of ethylene glycol, 4 mg. of p-toluenesulfonic acid, and 10 ml. of benzene are agitated for 1.5 hours with the use of a water trap at reflux temperature. The mixture is cooled, diluted with ether, shaken once with 4% sodium bicarbonate solution, washed neutral with water, dried over magnesium sulfate, and evaporated under vacuum, thus obtaining 390 mg. of the ketal as a colorless oil.

IR: 3500, 2945, 2882, 1708, 1604, 1588, 1280, 948 cm$^{-1}$.

1(q)

(1R,5S,6R,7R)-3,3-Ethylenedioxy-7-benzoyloxy-6-formylbicyclo[3,3,0]octane

Under agitation at 5°, a solution of 1.03 g. of the ketal prepared according to Reference Example 1(p) in 32 ml. of absolute methylene chloride is added dropwise to a solution of 5.4 g. of Collins reagent in 63 ml. of absolute methylene chloride; the mixture is stirred for 20 minutes at 5°. Then the mixture is diluted with ether, shaken three times with sodium bicarbonate solution and three times with brine, dried over magnesium sulfate, and evaporated under vacuum at 25°, thus obtaining 840 mg. of the aldehyde as a yellow oil.

IR: 2960, 2730, 1720, 1603, 1588, 1275, 948 cm$^{-1}$.

EXAMPLE 1

5-{(E)-(1S,5S,6R,7R)-7-Hydroxy-6-[(E)-3α-hydroxy-1-octenyl]bicyclo[3,3,0]octan-3-ylidene}-pentanoic Acid At 15° under argon, 12 ml. of a 1.04-molar solution of methylsulfinylmethyl sodium in DMSO is added dropwise to a solution of 3.04 g. of 4-carboxybutyltriphenylphosphonium bromide in 6 ml. of dry dimethyl sulfoxide (DMSO). The mixture is stirred for 30 minutes at room temperature. A solution of 495 mg. of (1R,5S,6R,7R)-7-(tetrahydropyran-2-yloxy)-6-[(E)-(3S)-3-(tetrahydropyran-2-yloxy)-1-octenyl]bicyclo[3,3,0]octan-3-one in 3 ml. of absolute DMSO is added dropwise to the red ylene solution, and the reaction mixture is stirred for 2 hours at 45°, whereafter it is poured on ice water, acidified to pH 4–5 with 10% citric acid solution, and extracted three times with methylene chloride. The organic phase is shaken with brine, dried over magnesium sulfate, and evaporated under vacuum. Chromatography of the residue on silica gel yields, with ether/pentane (3+2), 462 mg. of the olefin-formation product which, to split off the blocking groups, is stirred with 15 ml. of a mixture of acetic acid/water/tetrahydrofuran (65/35/10) for 20 hours at 25°. The mixture is evaporated under vacuum and the residue chromatographed on silica gel. With methylene chloride/isopropanol (95+5), the initial yield is 65 mg. of 5-{(Z)-(1S,5S,6R,7R)-7-Hydroxy-6-[(E)-(3S)-3-hydroxy-1-octenyl]bicyclo[3,3,0]octan-3-ylidene}-pentanoic acid (m.p. 95°), as well as, in the form of the more polar component, 103 mg. of the title compound as a colorless oil.

IR: 3600, 3450 (broad), 2940, 2865, 1712, 1604, 975 cm$^{-1}$.

The starting material for the above title compound is prepared as follows:

1(a)
(1R,5S,6R,7R)-3,3-Ethylenedioxy-7-benzoyloxy-6-[(E)-3-oxo-1-octenyl]bicyclo[3,3,0]octane At room temperature a solution of 664 mg. of 2-oxoheptylphosphonic acid dimethyl ester in 5.5 ml. of dimethoxyethane (DME) absolute is added dropwise to a suspension of 126 mg. of sodium hydride (55% suspension in oil) in 11 ml. of DME absolute. The mixture is agitated for 10 minutes, then 121 mg. of lithium chloride is added thereto, and the mixture is stirred for 2 hours at room temperature under argon. Then the mixture is combined at −20° with a solution of 755 mg. of the aldehyde prepared according to Reference Example 1(q) in 11 ml. of DME (absolute), and the mixture is stirred for 2.5 hours at room temperature under argon. Thereafter the reaction mixture is poured on 120 ml. of saturated ammonium chloride solution, extracted three times with ether, the organic extract is washed neutral with water, dried over magnesium sulfate, and evaporated under vacuum. The residue is purified by chromatography on silica gel. With ether/pentane (1+1), 795 mg. of the title compound is obtained as a colorless oil.
IR: 2940, 2862, 1715, 1670, 1628, 1275, 979, 948 cm$^{-1}$.

1(b)
(1R,5S,6R,7R)-3,3-Ethylenedioxy-7-benzoyloxy-6-[(E)-3α-hydroxy-1-octenyl]bicyclo[3,3,0]octane At −40° 420 mg. of sodium borohydride is added in incremental portions to a solution of 790 mg. of the ketone prepared according to Example 1(a) in 24 ml. of methanol, and the mixture is stirred under argon at −40° for one hour. Then the mixture is diluted with ether, washed neutral with water, dried over magnesium sulfate, and evaporated under vacuum. By column chromatography on silica gel with ether/pentane (7+3), 245 mg. of the title compound is initially obtained as a colorless oil. As the more polar component, 152 mg. of (1R,5S,6R,7R)-3,3-ethylenedioxy-7-benzoyloxy-6-[(E)-(3R)-3-hydroxy-1-octenyl]bicyclo[3,3,0]octane is produced.
IR: 3610, 3400 (broad), 2940, 1715, 1604, 1588, 1279, 971, 948 cm$^{-1}$.

1(c)
(1R,5S,6R,7R)-3,3-Ethylenedioxy-7-hydroxy-6-[(E)-3α-hydroxy-1-octenyl]bicyclo[3,3,0]octane A mixture of 500 mg. of the α-alcohol prepared according to Example 1(b) and 333 mg. of potassium carbonate (anhydrous) in 35 ml. of methanol is agitated for 16 hours at room temperature under argon. The mixture is then concentrated under vacuum, diluted with ether, and washed neutral with brine. The mixture is dried over magnesium sulfate and evaporated under vacuum, thus obtaining 495 mg. of the title compound as a colorless oil (crude product).
IR: 3600, 3450 (broad), 2940, 975, 948 cm$^{-1}$.

1(d)
(1R,5S,6R,7R)-7-Hydroxy-6-[(E)-3α-hydroxy-1-octenyl]bicyclo[3,3,0]octan-3-one 495 mg. of the diol prepared according to Example 1(c) is agitated for 22 hours with 18 ml. of a mixture of acetic acid/tetrahydrofuran/water (65/10/35). The mixture is then evaporated under vacuum while adding toluene, the residue is dissolved in methylene chloride, shaken twice with brine, dried over magnesium sulfate, and evaporated under vacuum. The residue is chromatographed on silica gel with ethyl acetate/pentane (9+1), thus obtaining 282 mg. of the title compound as a colorless oil.
IR: 3660, 3610, 2940, 2870, 1739, 973 cm$^{-1}$.

1(e)
(1R,5S,6R,7R)-7-(Tetrahydropyran-2-yloxy)-6-[(E)-3α-(tetrahydropyran-2-yloxy)-1-octenyl]bicyclo[3,3,0]octan-3-one A solution of 260 mg. of the ketone prepared according to Example 1(d), 0.36 ml. of dihydropyran, and 2.5 mg. of p-toluenesulfonic acid in 11 ml. of methylene chloride is agitated for 20 minutes at 5°. Then the mixture is diluted with ether, shaken with 4% sodium bicarbonate solution, washed neutral with water, dried over magnesium sulfate, and evaporated under vacuum, thus obtaining 490 mg. of the bis(tetrahydropyranyl) ether which is used without further purification for the Wittig reaction.
IR: 2955, 2862, 1739, 970 cm$^{-1}$.

EXAMPLE 2
5-{(E)-(1S,5S,6R,7R)-7-Hydroxy-6-[(E)-(4RS)-3α-hydroxy-4-methyl-1-octenyl]bicyclo[3,3,0]octan-3-ylidene}-pentanoic Acid At 15° under argon, 24 ml. of a 1.04-molar solution of methylsulfinylmethyl sodium in DMSO is added dropwise to 6.1 g. of 4-carboxybutyltriphenylphosphonium bromide in 12 ml. of DMSO absolute, and the mixture is agitated for 30 minutes at room temperature. A solution of 0.95 g. of (1R,5S,6R,7R)-7-tetrahydropyran-2-yloxy)-6-[(E)-(4RS)-4-methyl-3α-(tetrahydropyran-2-yloxy)-1-octenyl]bicyclo[3,3,0]octan-3-one in 6 ml. of absolute DMSO is added dropwise to the red ylene solution and the mixture is agitated for 2 hours at 45°. The reaction mixture is poured on ice water, acidified to pH 4–5 with 10% citric acid solution, and extracted three times with methylene chloride. The organic phase is shaken with brine, dried over magnesium sulfate, and evaporated under vacuum. Chromatography of the residue on silica gel yields, with ether/pentane (3+2), 0.89 g. of the olefin-formation product, which is stirred with 28 ml. of a mixture of acetic acid/water/tetrahydrofuran (65/35/10) to split off the blocking groups. The product is evaporated under vacuum and the residue chromatographed on silica gel. With methylene chloride/isopropanol (95+5), 142 mg. of 5-{(Z)-(1S,5S,6R,7R)-7-hydroxy-6-[(E)-(4RS)-3α-hydroxy-4-methyl-1-octenyl]bicyclo[3,3,0]octan-3-ylidene}-pentanoic acid is initially obtained, and, as the more polar component, 230 mg. of the title compound is produced as a colorless oil.
IR: 3610, 3440 (broad), 2940, 2860, 1712, 976 cm$^{-1}$.

The starting material for the above title compound is prepared as follows:

2(a)
(1R,5S,6R,7R)-3,3-Ethylenedioxy-7-benzoyloxy-6-[(E)-(4RS)-4-methyl-3-oxo-1-octenyl]bicyclo[3,3,0]octane Analogously to Example 1(a), 1.62 g. of the title compound is obtained as a colorless oil from 1.5 g. of the aldehyde prepared according to Reference Example 1(q) and 1.3 g. of 3-methyl-2-oxoheptanephosphonic acid dimethyl ester.
IR: 2940, 2860, 1715, 1672, 1628, 1275, 978, 948 cm$^{-1}$.

2(b)
(1R,5S,6R,7R)-3,3-Ethylenedioxy-7-benzoyloxy-6-[(E)-(4RS)-3α-hydroxy-4-methyl-1-octenyl]bicyclo[3,3,0]octane At −40° 850 mg. of sodium borohydride is added in incremental portions to a solution of 1.50 g. of the ketone prepared according to Example 2(a) in 48 ml. of methanol; the mixture is stirred for one hour at −40° under argon. The mixture is then diluted with ether, washed neutral with water, dried over magnesium sulfate, and evaporated under vacuum. By column chromatography on silica gel with ether/pentane (7+3), 520 mg. of the title compound (3α-hydroxy) is initially obtained and, as the more polar component, 320 mg. of isomeric 3β-hydroxy-configured compound is produced.

IR: 3600, 3420 (broad), 2940, 1715, 1603, 1588, 1278, 972, 948 cm$^{-1}$.

2(c)
(1R,5S,6R,7R)-3,3-Ethylenedioxy-7-hydroxy-6-[(E)-(4RS)-3α-hydroxy-4-methyl-1-octenyl]bicyclo[3,3,0]octane A mixture of 510 mg. of the α-alcohol prepared according to Example 2(b) and 330 mg. of potassium carbonate in 35 mg. of methanol is agitated for 18 hours at room temperature under argon. The mixture is then concentrated under vacuum, diluted with ether, and washed neutral with brine. Then, the mixture is dried over magnesium sulfate and evaporated under vacuum, yielding 485 mg. of the title compound as a colorless oil (crude product).

IR: 3600, 3430 (broad), 2945, 976, 948 cm$^{-1}$.

2(d)
(1R,5S,6R,7R)-Hydroxy-6-[(E)-(4RS)-3α-hydroxy-4-methyl-1-ocetnyl]bicyclo[3,3,0]octan-3-one Analogously to Example 1(d), 485 mg. of the diol produced according to Example 2(c) yields 295 mg. of the title compound as an oil.

IR: 3600, 3400 (broad), 2940, 2865, 1740, 973 cm$^{-1}$.

2(e)
(1R,5S,6R,7R)-7-(Tetrahydropyran-2-yloxy)-6-[(E)-(4RS)-4-methyl-3α-(tetrahydropyran-2-yloxy)-1-octenyl]bicyclo[3,3,0]octan-3-one Analogously to Example 1(e), 280 mg. of the ketone prepared according to Example 2(d) yields 460 mg. of the bis(tetrahydropyranyl) ether, which is used for the Wittig reaction without further purification.

IR: 2960, 2860, 1740, 972 cm$^{-1}$.

EXAMPLE 3
5-{(E)-(1S,5S,6R,7R)-7-Hydroxy-6-[(E)-(4RS)-4-fluoro-3α-hydroxy-1-octenyl]bicyclo[3,3,0]octan-3-ylidene}-pentanoic Acid At 15° under argon 18 ml. of a 1.04-molar solution of methylsulfinylmethyl sodium in DMSO is added dropwise to a solution of 4.55 g. of 4-carboxybutyltriphenylphosphonium bromide in 10 ml. of absolute DMSO, and the mixture is stirred for 30 minutes at room temperature. A solution of 745 mg. of (1R,5S,6R,7R)-7-tetrahydropyran-2-yloxy)-6-[(E)-(4RS)-4-fluoro-3α-(tetrahydropyran-2-yloxy)-1-octenyl]bicyclo[3,3,0]octan-3-one in 5 ml. of absolute DMSO is added dropwise to the red ylene solution, and the mixture is agitated for 2 hours at 45°. The reaction mixture is poured on ice water, acidified to pH 4–5 with 10% citric acid solution, and extracted three times with methylene chloride. The organic phase is taken with brine, dried over magnesium sulfate, and evaporated under vacuum. Chromatography of the residue on silica gel yields, with ether/pentane (3+2), 620 mg. of the olefin-formation product which is agitated, to split off the blocking groups, with 22 ml. of a mixture of acetic acid/water/tetrahydrofuran (65/35/10) for 20 hours at 25°. The mixture is evaporated under vacuum and the residue chromatographed on silica gel. With methylene chloride/isopropanol (95+5), the initial product is 122 mg. of 5-{(Z)-(1S,5S,6R,7R)-7-hydroxy-6-[(E)-(4RS)-4-fluoro-3α-hydroxy-1-octenyl]bicyclo[3,3,0]octan-3-ylidene}-pentanoic acid as well as, in the form of the more polar component, 208 mg. of the title compound as a colorless oil.

IR: 3600, 3440 (broad), 2945, 2860, 1713, 976 cm$^{-1}$.

The starting material for the above title compound is prepared as follows:

3(a)
(1R,5S,6R,7R)-3,3-Ethylenedioxy-7-benzoyloxy-6-[(E)-(4RS)-4-fluoro-3-oxo-1-octenyl]bicyclo[3,3,0]octane Analogously to Example 1(a), 765 mg. of the aldehyde prepared according to Reference Example 1(q) and 665 mg. of 3-fluoro-2-oxoheptanephosphonic acid dimethyl ester yield 620 mg. of the title compound as a colorless oil.

IR: 2945, 2860, 1715, 1670, 1630, 1276, 979, 948 cm$^{-1}$.

3(b)
(1R,5S,6R,7R)-3,3-Ethylenedioxy-7-benzoyloxy-6-[(E)-(4RS)-4-fluoro-3α-hydroxy-1-ocetnyl]bicyclo[3,3,0]octane Analogously to Example 1(b), 410 mg. of the ketone produced according to Example 3(a) and 230 mg. of sodium borohydride yield 146 mg. of the title compound as a colorless oil.

IR: 3600, 3410 (broad), 2945, 2865, 1715, 1604, 1590, 1278, 974, 948 cm$^{-1}$.

3(c)
(1R,5S,6R,7R)-3,3-Ethylenedioxy-7-hydroxy-6-[(E)-(4RS)-4-fluoro-3α-hydroxy-1-octenyl]bicyclo[3,3,0]octane In analogy to Example 1(c), 525 mg. of the α-alcohol prepared according to Example 3(b) and 340 mg. of potassium carbonate yield 490 mg. of the title compound as an oil.

IR: 3600, 3400 (broad), 2950, 2865, 976, 948 cm$^{-1}$.

3(d)
(1R,5S,6R,7R)-7-Hydroxy-6-[(E)-(4RS)-4-fluoro-3α-hydroxy-1-octenyl]bicyclo[3,3,0]octan-3-one Analogously to Example 1(d), 470 mg. of the diol prepared according to Example 3(c) yields 285 mg. of the title compound in the form of an oil.

IR: 3600, 3420 (broad), 2945, 2865, 1740, 975 cm$^{-1}$.

3(e)
(1R,5S,6R,7R)-7-(Tetrahydropyran-2-yloxy)-6-[(E)-(4RS)-4-fluoro-3α-(tetrahydropyran-2-yloxy)-1-octenyl]bicyclo[3,3,0]octan-3-one Analogously to Example 1(e), 285 mg. of the ketone produced by following Example 3(d) yields 470 mg. of the bis(tetrahydropyranyl) ether (crude product) which is used for the Wittig reaction without further purification.

IR: 2960, 2860, 1740, 975 cm$^{-1}$.

EXAMPLE 4

5-{(E)-(1S,5S,6R,7R)-7-Hydroxy-6-[(E)-3α-hydroxy-4,4-methylene-1-octenyl]bicyclo[3,3,0]octan-3-ylidene}-pentanoic Acid At 15° under argon, 36 ml. of a 1.04-molar solution of methylsulfinylmethyl sodium in DMSO is added dropwise to 9.2 g. of 4-carboxybutyltriphenylphosphonium bromide in 20 ml. of absolute DMSO, and the mixture is agitated for 30 minutes at room temperature. A solution of 1.45 g. of (1R,5S,6R,7R)-7-tetrahydropyran-2-yloxy)-6-[(E)-4,4-methylene-3α-(tetrahydropyran-2-yloxy)-1-octenyl]bicyclo[3,3,0]octan-3-one in 10 ml. of DMSO is added dropwise to the red ylene solution, and the mixture is stirred for 2 hours at 45°. The reaction mixture is poured on ice water, acidified to pH 5 with 10% citric acid solution, and extracted three times with methylene chloride. The organic phase is shaken with brine, dried over magnesium sulfate, and evaporated under vacuum. Chromatography of the residue on silica gel yields, with ether/pentane (3+2), 1.38 g. of the olefin-formation product which, to split off the blocking groups, is stirred with 35 ml. of a mixture of acetic acid/water/tetrahydrofuran (65/35/10). The mixture is then evaporated under vacuum and the residue chromatographed on silica gel. With methylene chloride/isopropanol (95+5), the initial product is 210 mg. of 5-{(Z)-(1S,5S,6R,7R)-7-hydroxy-6-[(E)-3α-hydroxy-4,4-methylene-1-octenyl[bicyclo[3,3,0]octan-3-ylidene}-pentanoic acid, and, as the more polar component, 295 mg. of the title compound is obtained as a colorless oil.

IR: 3600, 3450 (broad), 2945, 2865, 1712, 976 cm$^{-1}$.

The starting material for the above title compound is prepared as follows:

4(a)
(1R,5S,6R,7R)-3,3-Ethylenedioxy-7-benzoyloxy-6-[(E)-4,4-methylene-3-oxo-1-octenyl]bicyclo[3,3,0]octane Analogously to Example 1(a), 1.48 g. of the aldehyde produced according to Reference Example 1(q) and 1.3 g. of 3,3-methylene-2-oxoheptanephosphonic acid dimethyl ester yield 1.55 g. of the title compound as a colorless oil.

IR: 2940, 2860, 1715, 1670, 1630, 1275, 978 cm$^{-1}$.

4(b)
(1R,5S,6R,7R)-3,3-Ethylenedioxy-7-benzoyloxy-6-[(E)-3α-hydroxy-4,4-methylene-1-octenyl]bicyclo[3,3,0]octane In analogy to Example 1(b), 1.45 g. of the ketone prepared according to Example 4(a) and 850 mg. of sodium borohydride yield 510 mg. of the title compound as a colorless oil.

IR: 3600, 3400 (broad), 2945, 2860, 1715, 1603, 1590, 1277, 973, 948 cm$^{-1}$.

4(c)
(1R,5S,6R,7R)-3,3-Ethylenedioxy-7-hydroxy-6-[(E)-3α-hydroxy-4,4-methylene-1-octenyl]bicyclo[3,3,0]octane Analogously to Example 1(c), 490 mg. of the α-alcohol prepared according to Example 4(b) and 320 mg. of potassium carbonate yield 470 mg. of the title compound as a colorless oil.

IR: 3600, 3400 (broad), 2940, 2860, 976 cm$^{-1}$.

4(d)
(1R,5S,6R,7R)-7-Hydroxy-6-[(E)-3α-hydroxy-4,4-methylene-1-octenyl]bicyclo[3,3,0]octan-3-one Analogously to Example 1(d), 470 mg. of the diol prepared according to Example 4(c) produces 280 mg. of the title compound as an oil.

IR: 3600, 3400 (broad), 2945, 2860, 1740, 974 cm$^{-1}$.

4(e)
(1R,5S,6R,7R)-7-(Tetrahydropyran-2-yloxy)-6-[(E)-4,4-methylene-3α-(tetrahydropyran-2-yloxy)-1-octenyl]bicyclo[3,3,0]octan-3-one In analogy to Example 1(e), 270 mg. of the ketone prepared according to Example 4(d) yields 440 mg. of the bis(tetrahydropyranyl) ether which is used for the Wittig olefin-forming reaction without further purification.

IR: 2960, 2860, 1739, 975 cm$^{-1}$.

EXAMPLE 5

5-{(E)-(1S,5S,6R,7R)-7-Hydroxy-6-[(E)-3α-hydroxy-1-nonenyl]bicyclo[3,3,0]octan-3-ylidene}-pentanoic Acid At 15° under argon, 13.2 ml. of a 1.04-molar solution of methylsulfinylmethyl sodium in DMSO is added dropwise to a solution of 3.34 g. of 4-carboxybutyltriphenylphosphonium bromide in 6.5 ml. of absolute DMSO. After 15 minutes, a solution of 500 mg. of (1R,5S,6R,7R)-7-(tetrahydropyran-2-yloxy)-6-[(E)-3α-(tetrahydropyran-2-yloxy)-1-nonenyl]bicyclo[3,3,0]octan-3-one in 3 ml. of absolute DMSO is added dropwise to this ylene solution, and the mixture is heated for 2 hours to 45°-50°. The mixture is then poured on ice water, acidified to pH 5 with citric acid, and extracted with methylene chloride. The extract is shaken with brine, dried over magnesium sulfate, and evaporated under vacuum. Chromatography of the residue on silica gel with ether/pentane mixtures yields 435 mg. of a yellow oil, which is agitated to split off the blocking groups with 15 ml. of a mixture of acetic acid/water/tetrahydrofuran (65/35/10) for 16 hours at 40°. After evaporation of the solution, the residue is chromatographed on silica gel with methylene chloride/isopropanol (95+5). Yield: 80 mg. of 5-{(Z)-(1S,5S,6R,7R)-7-hydroxy-6-[(E)-3α-hydroxy-1-nonenyl]bicyclo[3,3,0]octan-3-ylidene}-pentanoic acid and, as the more polar component, 120 mg. of the title compound as a colorless, viscous oil.

IR: 3600, 3455 (broad), 2945, 2865, 1710, 978 cm$^{-1}$.

The starting material for the title compound is produced as described below:

5(a)
(1R,5S,6R,7R)-3,3-Ethylenedioxy-7-benzoyloxy-6-[(E)-3-oxo-1-nonenyl]bicyclo[3,3,0]octane 252 mg. of sodium hydride (55% strength) is suspended in 25 ml. of absolute dimethoxyethane, and at 15° 1.39 g. of 2-oxooctylphosphonic acid dimethyl ester dissolved in 10 ml. of dimethoxyethane is added dropwise thereto. The mixture is stirred for 10 minutes, combined with 245 mg. of lithium chloride, and, after one hour at −20°, a solution of 1.51 g. of the aldehyde prepared according to Reference Example 1(q) in 25 ml. of absolute dimethoxyethane is added dropwise thereto.

The mixture is then stirred for 2 hours at 10°–15°, poured on 250 ml. of saturated ammonium chloride solution, extracted repeatedly with ether, the organic extract washed with brine, dried over magnesium sulfate, and evaporated under vacuum. The residue is purified by chromatography on silica gel with ether/hexane mixtures. Yield: 1.49 g. of the above-mentioned ketone in the form of an oil.

IR: 2945, 2860, 1715, 1670, 1630, 1275, 978, 948 cm$^{-1}$.

5(b)
(1R,5S,6R,7R)-3,3-Ethylenedioxy-7-benzoyloxy-6-[(E)-3α-hydroxy-1-nonenyl]bicyclo[3,3,0]octane Under agitation at −40°, 800 mg. of sodium borohydride is added in incremental portions to a solution of 1.44 g. of the ketone prepared according to Example 5(a) in 40 ml. of methanol; the mixture is stirred for one hour at −40°, diluted with 200 ml. of ether, washed neutral with brine, dried over magnesium sulfate, and evaporated under vacuum. The mixture of the epimeric alcohols is separated by chromatography on silica gel with hexane/ether mixtures, thus obtaining as the nonpolar component 576 mg. of the desired (3S)-alcohol as an oil, as well as, in the form of the more polar component, 490 ml. of the (3R)-alcohol, likewise as an oil.

IR: 3600, 3400 (broad), 2945, 1715, 1602, 1588, 1275, 975, 948 cm$^{-1}$.

5(c)
(1R,5S,6R,7R)-3,3-Ethylenedioxy-7-hydroxy-6-[(E)-3α-hydroxy-1-nonenyl]bicyclo[3,3,0]octane 500 mg. of the (3S)-alcohol from Example 5(b) is stirred in 35 ml. of methanol with 315 mg. of potassium carbonate for 16 hours at 20°. After concentration under vacuum, the mixture is diluted with 200 ml. of ether, washed neutral with water, dried over magnesium sulfate, and evaporated under vacuum. The crude product is used in the next stage without further purification.

5(d)
(1R,5S,6R,7R)-7-Hydroxy-6-[(E)-3α-hydroxy-1-nonenyl]bicyclo[3,3,0]octan-3-one The crude product from Example 5(c) is stirred for 22 hours with 20 ml. of a mixture of acetic acid/water/tetrahydrofuran (65/35/10), evaporated under vacuum with the addition of toluene, and the residue is chromatographed on silica gel with ethyl acetate/hexane mixtures, thus obtaining 270 mg. of the above-mentioned ketone as an oil.

IR: 3600, 2945, 2870, 1740, 975 cm$^{-1}$.

5(e)
(1R,5S,6R,7R)-7-(Tetrahydropyran-2-yloxy)-6-[(E)-3α-(tetrahydropyran-2-yloxy)-1-nonenyl]bicyclo[3,3,0]octan-3-one 250 mg. of the ketone from Example 5(d) is stirred in 10 ml. of methylene chloride with 0.35 ml. of dihydropyran and 2.5 mg. of p-toluenesulfonic acid for 30 minutes at 0°–5°. Thereafter the mixture is diluted with 100 ml. of methylene chloride, shaken with sodium bicarbonate solution and brine, dried over magnesium sulfate, and evaporated under vacuum, thus obtaining 475 mg. of the bis(tetrahydropyranyl) ether as a yellow oil.

IR: 2955, 2860, 1740, 972 cm$^{-1}$.

EXAMPLE 6
5-{(E)-(1S,5S,6R,7R)-7-Hydroxy-6-[(E)-(4RS)-3α-hydroxy-4-methyl-1-nonenyl]bicyclo[3,3,0]octan-3-ylidene}-pentanoic Acid Analogously to Example 5, 420 mg. of (1R,5S,6R,7R)-7-(tetrahydropyran-2-yloxy)-6-[(E)-(4RS)-4-methyl-3α-(tetrahydropyran-2-yloxy)-1-nonenyl]bicyclo[3,3,0]-octan-3-one yields 95 mg. of the title compound and 85 mg. of the Z-isomer 5-{(Z)-(1S,5S,6R,7R)-7-hydroxy-6-[(E)-(4RS)-3α-hydroxy-4-methyl-1-nonenyl]bicyclo[3,3,0]octan-3-ylidene}-pentanoic acid.

IR (E-isomers): 3600, 3450 (broad), 2945, 2860, 1710, 978 cm$^{-1}$.

The starting material for the title compound is produced as follows:

6(a)
(1R,5S,6R,7R)-3,3-Ethylenedioxy-7-benzoyloxy-6-[(E)-4-methyl-3-oxo-1-nonenyl]bicyclo[3,3,0]octane In analogy to Example 5(a), 2 g. of (1R,5S,6R,7R)-3,3-ethylenedioxy-7-benzoyloxy-6-formylbicyclo[3,3,0]octane yields, with the 3-methyl-2-oxooctylphosphonic acid dimethyl ester, 2.01 g. of the above-mentioned ketone as a viscous oil.

IR: 2950, 2860, 1715, 1670, 1630, 1602, 1275, 978, 948 cm$^{-1}$.

6(b)
(1R,5S,6R,7R)-3,3-Ethylenedioxy-7-benzoyloxy-6-[(E)-(4RS)-3α-hydroxy-4-methyl-1-nonenyl]bicyclo[3,3,0]octane Analogously to Example 5(b), 1.95 g. of the ketone prepared according to Example 6(a) yields 800 mg. of the above (3R)-α-alcohol and, as the more polar component, 730 mg. of the (3S)-β-alcohol.

IR: 3600, 3400 (broad), 2950, 1715, 1602, 1588, 1270, 978, 948 cm$^{-1}$.

6(c)
(1R,5S,6R,7R)-3,3-Ethylenedioxy-7-hydroxy-6-[(E)-(4RS)-3α-hydroxy-4-methyl-1-nonenyl]bicyclo[3,3,0]octane In analogy to Example 5(c), 790 mg. of the (3R)-α-alcohol prepared according to Example 6(b) yields 750 mg. of the above diol as a crude product.

6(d)
(1R,5S,6R,7R)-7-Hydroxy-6-[(E)-(4RS)-3α-hydroxy-4-methyl-1-nonenyl]bicyclo[3,3,0]octan-3-one Analogously to Example 5(d), 730 mg. of the diol prepared according to Example 6(c) yields 420 mg. of the above ketone as a colorless oil.

IR: 3600, 2950, 2870, 1740, 978 cm$^{-1}$.

6(e)
(1R,5S,6R,7R)-7-(Tetrahydropyran-2-yloxy)-6-[(E)-(4RS)-4-methyl-3α-(tetrahydropyran-2-yloxy)-1-nonenyl]bicyclo[3,3,0]octan-3-one Analogously to Example 5(e), 700 mg. of the ketone prepared as in Example 6(d) yields 950 mg. of the above bis(tetrahydropyranyl) ether as an oil.

IR: 2950, 2860, 1740, 978 cm$^{-1}$.

EXAMPLE 7

5-{(E)-(1S,5S,6R,7R)-7-Hydroxy-6-[(E)-3α-hydroxy-4-phenyl-1-butenyl]bicyclo[3,3,0]octan-3-ylidene}-pentanoic Acid A solution of 2.21 g. of 4-carboxybutyltriphenylphosphonium bromide in 5 ml. of absolute DMSO is combined at 15° with 9.5 ml. of a 1.04-molar solution of methylsulfinylmethyl sodium in DMSO. After 15 minutes, 440 mg. of (1R,5S,6R,7R)-7-(tetrahydropyran-2-yloxy)-6-[(E)-4-phenyl-3α-(tetrahydropyran-2-yloxy)-1-butenyl]bicyclo[3,3,0]-octan-3-one, dissolved in 3 ml. of absolute DMSO, is added to the reaction mixture, and the latter is stirred for 2 hours at 50°, then poured on ice water, and adjusted to pH 4.5 with citric acid. The mixture is extracted with methylene chloride, the extract is shaken with brine, dried over magnesium sulfate, and evaporated under vacuum. After purification by chromatography on silica gel with hexane/ether mixtures, the product is reacted with acetic acid to split off the blocking groups (analogously to Example 5). Purification by chromatography on silica gel with methylene chloride/isopropanol (95+5) produces 75 mg. of 5-{(Z)-(1S,5S,6R,7R)-7-hydroxy-6-[(E)-3α-hydroxy-4-phenyl-1-butenyl]bicyclo[3,3,0]octan-3-ylidene-}-pentanoic acid and, as the more polar component, 110 mg. of the title compound as a colorless oil.

IR: 3600, 3450 (broad), 2945, 2860, 1710, 1602, 978 cm$^{-1}$.

The starting material for the title compound is prepared as follows:

7(a)
(1R,5S,6R,7R)-3,3-Ethylenedioxy-7-benzoyloxy-6-[(E)-3-oxo-4-phenyl-1-butenyl]bicyclo[3,3,0]octane In analogy to Example 5(a), 2.5 g. of (1R,5S,6R,7R)-3,3-ethylenedioxy-7-benzoyloxy-6-formylbicyclo[3,3,0]octane produces, by reaction with the sodium salt of 2-oxo-3-phenylpropylphosphonic acid dimethyl ester, 2.45 g. of the above ketone as an oil.

IR: 2955, 2870, 1712, 1670, 1632, 1600, 1275, 975, 948 cm$^{-1}$.

7(b)
(1R,5S,6R,7R)-3,3-Ethylenedioxy-7-benzoyloxy-6-[(E)-3α-hydroxy-4-phenyl-1-butenyl]bicyclo[3,3,0]octane Analogously to Example 5(b), 2.40 g. of the ketone prepared according to Example 7(a) yields 1.05 g. of the above (3S)-α-alcohol and, as the more polar component, 0.95 g. of the (3R)-β-alcohol.

IR: 3600, 3400 (broad), 2950, 2865, 1712, 1602, 1588, 1270, 978, 948 cm$^{-1}$.

7(c)
(1R,5S,6R,7R)-3,3-Ethylenedioxy-7-hydroxy-6-[(E)-3α-hydroxy-4-phenyl-1-butenyl]bicyclo[3,3,0]octane Analogously to Example 5(c), 1.02 g. of the (3S)-α-alcohol prepared according to Example 7(b) yields 800 mg. of the above diol as a crude product.

7(d)
(1R,5S,6R,7R)-7-Hydroxy-6-[(E)-3α-hydroxy-4-phenyl-1-butenyl]bicyclo[3,3,0]octan-3-one In analogy to Example 5(d), 800 mg. of the diol prepared according to Example 7(c) yields 530 mg. of the above ketone as a colorless oil.

IR: 3600, 2950, 2865, 1738, 1602, 975 cm$^{-1}$.

7(e)
(1R,5S,6R,7R)-7-(Tetrahydropyran-2-yloxy)-6-[(E)-4-phenyl-3α-(tetrahydropyran-2-yloxy)-1-butenyl]bicyclo[3,3,0]octan-3-one Analogously to Example 5(e), 500 mg. of the ketone prepared according to Example 7(d) yields 700 mg. of the above bis(tetrahydropyranyl) ether as an oil.

IR: 2950, 2860, 1738, 1602, 976 cm$^{-}$.

EXAMPLE 8

5-{(E)-(1S,5S,6R,7R)-7-Hydroxy-6-[(4RS)-3α-hydroxy-4-methyl-1-octyl]bicyclo[3,3,0]octan-3-ylidene}-pentanoic Acid An ylene solution, prepared from 3 g. of 4-carboxybutyltriphenylphosphonium bromide analogously to Example 5, is combined with 450 mg. of (1R,5S,6R,7R)-7-(tetrahydropyran-2-yloxy)-6-[(4RS)-4-methyl-3α-(tetrahydropyran-2-yloxy)-1-octyl]bicyclo[3,3,0]octan-3-one, dissolved in 3 ml. of absolute DMSO. The mixture is stirred for 2 hours at 50°, then diluted with ice water, acidified to pH 4.5 with citric acid, and extracted repeatedly with methylene chloride. The extracts are combined, shaken with brine, dried over magnesium sulfate, and evaporated under vacuum. To remove the blocking groups, the crude product is agitated for 6 hours at 45° with 20 ml. of a mixture of acetic acid/water/tetrahydrofuran (65/35/10). After evaporation to dryness, the residue is chromatographed on silica gel with methylene chloride/1–5% isopropanol. Yield: 80 mg. of 5-}(Z)-(1S,5S,6R,7R)-7-hydroxy-6-[(4RS)-3α-hydroxy-4-methyl-1-octyl]bicyclo[3,3,0]octan-3-ylidene}-pentanoic acid, and, as the more polar component, 110 mg. of the title compound as a colorless oil.

IR: 3600, 3450 (broad), 2950, 2860, 1710 cm$^{-1}$.

The starting material for the title compound is prepared as follows:

8(a)
(1R,5S,6R,7R)-7-(Tetrahydropyran-2-yloxy)-6-[(4RS)-4-methyl-3α-(tetrahydropyran-2-yloxy)-1-octyl]bicyclo[3,3,0]octan-3-one A solution of 1 g. of (1R,5S,6R,7R)-7-(tetrahydropyran-2-yloxy)-6-[(E)-(4RS)-4-methyl-3α-(tetrahydropyran-2-yloxy)-1-octenyl]bicyclo[3,3,0]-octan-3-one in 25 ml. of ethyl acetate is shaken with 100 mg. of palladium on charcoal (10%) under a hydrogen atmosphere for about one hour until 1 mole of hydrogen has been absorbed per mole of substrate. Filtration and evaporation of the solvent yields the above compound as a light-yellow oil.

IR: 2960, 2865, 1740 cm$^{-1}$.

EXAMPLE 9

5-[(E)-(1S,5S,6R,7R)-7-Hydroxy-6-(3α-hydroxy-1-nonyl)bicyclo[3,3,0]octan-3-ylidene]-pentanoic Acid An ylene solution, prepared from 3.5 g. of 4-carboxybutyltriphenylphosphonium bromide analogously to Example 5, is combined with 500 mg. of (1R,5S,6R,7R)-7-(tetrahydropyran-2-yloxy)-6-[3α-(tetrahydropyran-2-yloxy)-1-nonyl]bicyclo[3,3,0]octan-3-one, dissolved in 3 ml. of absolute DMSO. The mixture is stirred for 2 hours at 50°. After dilution with ice water and acidification to pH 4.5 with citric acid, the mixture is repeatedly extracted with methylene chloride. The combined extracts are shaken with brine, dried over magnesium sulfate, and evaporated under vacuum. To remove the blocking groups, the crude product is stirred for 6 hours at 45° with 20 ml. of a mixture of acetic acid/water/tetrahydrofuran (65/35/10). After evaporation to dryness the residue is chromatographed on silica gel with methylene chloride/1-5% isopropanol, thus obtaining 100 mg. of 5-[(Z)-(1S,5S,6R,7R)-7-hydroxy-6-(3α-hydroxy-1-nonyl)bicyclo[3,3,0]octan-3-ylidene]-pentanoic acid and, as the more polar component, 120 mg. of the title compound as a colorless oil.

IR: 3600, 3455 (broad), 2950, 2865, 1710 cm$^{-1}$.

The starting material for the title compound is obtained as follows:

9(a)
(1R,5S,6R,7R)-7-(Tetrahydropyran-2-yloxy)-6-[3α-(tetrahydropyran-2-yloxy)-1-nonyl]bicyclo[3,3,0]octan-3-one 800 mg. of (1R,5S,6R,7R)-7-(tetrahydropyran-2-yloxy)-6-[(E)-(3S)-3-(tetrahydropyran-2-yloxy)-1-nonenyl]-bicyclo[3,3,0]octan-3-one [prepared as set forth in Example 5(e)], dissolved in 20 ml. of ethyl acetate, is shaken with 80 mg. of palladium on charcoal (10%) under a hydrogen atmosphere until 1 mole of hydrogen has been absorbed per mole of substrate. After filtration and evaporation of the solvent, the above compound is obtained as an oil.

IR: 2965, 2865, 1740 cm$^{-1}$.

EXAMPLE 10
5-{(E)-(1S,5S,6R,7R)-7-Hydroxy-6-[(E)-3α-hydroxy-oct-1-en-6-inyl]bicyclo[3,3,0]octan-3-ylidene}-pentanoic Acid At 15° under argon, 10.6 ml. of a 1.04-molar solution of methylsulfinylmethyl sodium in DMSO is added dropwise to a solution of 2.66 g. of 4-carboxybutyltriphenylphosphonium bromide in 6 ml. of absolute DMSO. The mixture is stirred for 30 minutes at room temperature. A solution of 430 mg. of (1R,5S,6R,7R)-7-(tetrahydropyran-2-yloxy)-6-[(E)-3α-(tetrahydropyran-2-yloxy)oct-1-en-6-inyl]bicyclo[3,3,0]-octan-3-one in 3 ml. of absolute DMSO is added dropwise to the red ylene solution, and the mixture is agitated for 2 hours at 45°. The reaction mixture is poured on ice water, acidified to pH 4–5 with 10% citric acid solution, and extracted three times with methylene chloride. The organic phase is shaken with brine, dried over magnesium sulfate, and evaporated under vacuum. Chromatography of the residue on silica gel yields, with ether/pentane (3+2), 445 mg. of the olefin-formation product which, to split off the blocking groups, is stirred for 20 hours at 25° with 15 ml. of a mixture of acetic acid/water/tetrahydrofuran (65/35/10). The mixture is then evaporated under vacuum, and the residue is chromatographed on silica gel. With methylene chloride/isopropanol (95+5), the initial yield is 72 mg. of 5-{(E)-(1S,5S,6R,7R)-7-hydroxy-6-[(Z)-3α-hydroxyoct-1-en-6-inyl]bicyclo[3,3,0]octan-3-ylidene}-pentanoic acid and, as the more polar component, 121 mg. of the title compound as a colorless oil.

IR: 3600, 3420 (broad), 2945, 2860, 1712, 976 cm$^{-1}$.

The starting material for the above title compound is prepared as follows:

10(a)
(1R,5S,6R,7R)-3,3-Ethylenedioxy-7-benzoyloxy-6-[(E)-3-oxooct-1-en-6-inyl]bicyclo[3,3,0]octane Analogously to Example 1(a), 560 mg. of the aldehyde prepared according to Reference Example 1(q) and 0.5 g. of 2-oxohept-5-ynephosphonic acid dimethyl ester yield 0.62 g. of the title compound as a colorless oil.

IR: 2945, 2860, 1714, 1672, 1630, 1275, 978, 948 cm$^{-1}$.

10(b)
(1R,5S,6R,7R)-3,3,-Ethylenedioxy-7-benzoyloxy-6-[(E)-3α-hydroxyoct-1-en-6-inyl]bicyclo[3,3,0]octane Analogously to Example 1(b), 400 mg. of the ketone prepared according to Example 10(a) and 220 mg. of sodium borohydride yield 135 mg. of the title compound as a colorless oil.

IR: 3600, 3410 (broad), 2940, 2860, 1715, 1603, 1590, 1278, 972, 948 cm$^{-1}$.

10(c)
(1R,5S,6R,7R)-3,3-Ethylenedioxy-7-hydroxy-6-[(E)-3α-hydroxyoct-1-en-6-inyl]bicyclo[3,3,0]octane Analogously to Example 1(c), 240 mg. of the α-alcohol prepared according to Example 10(b) and 165 mg. of potassium carbonate yield 230 mg. of the title compound as a colorless oil (crude product).

IR: 3600, 3440 (broad), 2945, 2860, 974, 948 cm$^{-1}$.

10(d)
(1R,5S,6R,7R)-7-Hydroxy-6-[(E)-3α-hydroxy-oct-1-en-6-inyl]bicyclo[3,3,0]octan-3-one Analogously to Example 1(d), 230 mg. of the diol prepared according to Example 10(c) yields 141 mg. of the title compound as a colorless oil.

IR: 3640, 3610, 2945, 2965, 1740, 974 cm$^{-1}$.

10(e)
(1R,5S,6R,7R)-7-(Tetrahydropyran-2-yloxy)-6-[(E)-3α-(tetrahydropyran-2-yloxy)-oct-1-en-6-inyl]bicyclo[3,3,0]octan-3-one In analogy to Example 1(e), 130 mg. of the ketone prepared according to Example 10(d) and 0.18 ml. of dihydropyran yield 230 mg. of the bis(tetrahydropyranyl) ether which is utilized for the Wittig reaction without further purification.

IR: 2960, 2860, 1740, 972 cm$^{-1}$.

EXAMPLE 11
5-{(E)-(1S,5S,6R,7R)-7-Hydroxy-6-[(E)-(4RS)-3α-hydroxy-4-methyloct-1-en-6-inyl]bicyclo[3,3,0]octan-3-ylidene}-pentanoic Acid At 15° under argon, 21.3 ml. of a 1.04-molar solution of methylsulfinylmethyl sodium in DMSO is added dropwise to a solution of 5.3 g. of 4-carboxybutyltriphenylphosphonium bromide in 12 ml. of absolute DMSO. The mixture is stirred for 30 minutes at room temperature. A solution of 870 mg. of (1R,5S,6R,7R)-7-(tetrahydropyran-2-yloxy)-6-[(E)-(4RS)-4-methyl-3α-(tetrahydropyran-2-yloxy)oct-1-en-6-inyl]bicyclo[3,3,0]octan-3-one in 6 ml. of absolute DMSO is added dropwise to the red ylene solution, and the mixture is stirred for 2 hours at 45°. The reaction mixture is poured on ice water, acidified to pH 5 with 10% citric acid solution, and extracted three times with methylene chloride. The organic phase is shaken with brine, dried over mangnesium sulfate, and evaporated under vacuum. Chromatography of the residue on silica gel yields, with ether/pentane (3+2), 940 mg. of the olefin-formation product which, to split off the blocking groups, is agitated with 30 ml. of a mixture of acetic acid/water/tetrahydrofuran (65/35/10) for 20 hours at 25°. The mixture is evaporated under vacuum and the residue is chromatographed on silica gel. With methylene chloride/isopropanol (95+5), the yield is 165 mg. of 5{(Z)-(1S, 5S, 6R, 7R)-7-hydroxy-6-[(E)-(4RS)-3α-hydroxy-4-methyloct-1-en-6-inyl]bicyclo[3,3,0]octan-3-ylidene}-pentanoic acid, and as the more polar component 253 mg. of the title compound as a colorless oil.

IR: 3600, 3400 (broad), 2940, 2860, 1712, 975 cm$^{-1}$.

The starting material for the above title compound is prepared as follows:

11(a)
(1R,5S,6R,7R)-3,3-Ethylenedioxy-7-benzoyloxy-6-[(E)-(4RS)-4-methyl-3-oxooct-1-en-6-inyl]bicyclo[3,3,0]octane Analogously to Example 1(a), 1.3 g. of the aldehyde produced according to Reference Example 1(q) and 1 g. of 3-methyl-2-oxohept-5-ynephosphonic acid dimethyl ester yield 1.45 g. of the title compound as an oil.

IR: 2940, 2860, 1714, 1670, 1629, 1275, 978, 948 cm$^{-1}$.

11(b)
(1R,5S,6R,7R)-3,3-Ethylenedioxy-7-benzoyloxy-6-[(E)-(4RS)-3α-hydroxy-4-methyloct-1-en-6-inyl]bicyclo[3,3,0]octane Analogously to Example 1(b), 810 mg. of the ketone prepared according to Example 11(a) and 450 mg. of sodium borohydride yield 380 mg. of the title compound as a colorless oil.

IR: 3600, 3400 (broad), 2945, 2860, 1715, 1602, 1589, 1278, 973, 948 cm$^{-1}$.

11(c)
(1R,5S,6R,7R)-3,3-Ethylenedioxy-7-hydroxy-6-[(E)-(4RS)-3α-hydroxy-4-methyloct-1-en-6-inyl]bicyclo[3,3,0]octan-3-one In analogy to Example 1(c), 500 mg. of the α-alcohol obtained according to Example 11(b) and 340 mg. of potassium carbonate yield 465 mg. of the title compound as an oil (crude product).

IR: 3600, 3400 (broad), 2940, 2860, 976, 948 cm$^{-1}$.

11(d)
(1R,5S,6R,7R)-7-Hydroxy-6-[(E)-(4RS)-3α-hydroxy-4-methyloct-1-en-6-inyl]bicyclo[3,3,0]octan-3-one Analogously to Example 1(d), 455 mg. of the diol prepared according to Example 11(c) yields 295 mg. of the title compound as a colorless oil.

IR: 3600, 2945, 2860, 1740, 974 cm$^{-1}$.

11(e)
(1R,5S,6R,7R)-7-(Tetrahydropyran-2-yloxy)-6-[(E)-(4RS)-4-methyl-3α-(tetrahydropyran-2-yloxy)oct-1-en-6-inyl]bicyclo[3,3,0]octan-3-one In analogy to Example 1(e), 270 mg. of the ketone prepared according to Example 11(d) and 0.38 ml. of dihydropyran yield 460 mg. of the bis(tetrahydropyranyl) ether which is used for the Wittig reaction without further purification.

IR: 2960, 2865, 1738, 975 cm$^{-1}$.

EXAMPLE 12

5-{(E)-(1S,5S,6R,7R)-7-Hydroxy-6-[(E)-3,α,β-hydroxy-3-methyloct-1-en-6-inyl]bicyclo[3,3,0]octan-3-ylidene}-pentanoic Acid At 15° under argon, 6 ml. of a 1.04-molar solution of methylsulfinylmethyl sodium in DMSO is added dropwise to a solution of 1.50 g. of 4-carboxybutyltriphenylphosphonium bromide in 5 ml. of absolute DMSO. After 15 minutes the mixture is combined with 250 mg. of (1S,5S,6R,7R)-7-(tetrahydropyran-2-yloxy)-6-[(E)-3α,β-methyl-3-(tetrahydropyran-2-yloxy)oct-1-en-6-inyl]bicyclo[3,3,0]octan-3-one, dissolved in 3 ml. of absolute DMSO, and the mixture is stirred for 2 hours at 50°. After dilution with ice water and acidification with dilute citric acid solution to pH 4.5, the mixture is repeatedly extracted with methylene chloride, the extract is washed with brine, dried over magnesium sulfate, and evaporated under vacuum. After chromatography of the residue on silica gel, 270 mg. of a crude product is obtained with ether/pentane (1+1) which, for splitting off the blocking groups, is stirred for 20 hours at 25° with 8 ml. of a mixture of acetic acid/water/tetrahydrofuran (65/35/10). The mixture is evaporated under vacuum, and the residue is chromatographed on silica gel with methylene chloride/1–5% isopropanol, thus obtaining initially 35 mg. of 5-{(Z)-(1S,5S,6R,7R)-7-hydroxy-6-[(E)-3α,β-hydroxy-3-methyl-oct-1-en-6-inyl]bicyclo[3,3,0]octan-3-ylidene}-pentanoic acid and, as the more polar component, 55 mg. of the title compound as a colorless oil.

IR: 3600, 3420, (broad), 2950, 2865, 1710, 978 cm$^{-1}$.

The starting material for the above title compound is produced as follows:

12(a)
(1R,5S,6R,7R)-3,3-Ethylenedioxy-7-benzoyloxy-6-[(E)-3α,β-hydroxy-3-methyloct-1-en-6-inyl]bicyclo[3,3,-0]octane At −60°, 30 ml. of an ether solution of methylmagnesium bromide solution (prepared from 0.1 mole of magnesium) is added dropwise to a solution of 4 g. of (1R,5S,6R,7R)-3,3-ethylenedioxy-7-benzoyloxy-6-[(E)-3-oxo-oct-1-en-6-inyl]bicyclo[3,3,0]octane [preparation see Example 10(a)] in 150 ml. of absolute tetrahydrofuran. The mixture is agitated for 15 minutes and then poured in 200 ml. of saturated ammonium chloride solution. The reaction mixture is agitated for 10 minutes at 20°, extracted four times with respectively 75 ml. of ether, the combined extracts are washed twice with respectively 30 ml. of brine, dried over magnesium sulfate, and evaporated under vacuum. Purification by column chromatography on silica gel with hexane/ethyl acetate mixtures yields 3.5 g. of the above alcohol as an oil.

IR: 3600, 3450 (broad), 2960, 2865, 1715, 1602, 1588, 1275, 976, 948 cm$^{-1}$.

12(b):
(1R,5S,6R,7R)-3,3-Ethylenedioxy-7-hydroxy-6[(E)-3α,β-hydroxy-3-methyloct-1-en-6-inyl]bicyclo[3,3,-0]octane A solution of 3.3 g. of the alcohol prepared according to Example 12(a) in 300 ml. of methanol is agitated for 16 hours at 25° with 2.5 g. of potassium carbonate. Then the methanol is evaporated under vacuum, the residue is distributed between methylene chloride and water, the organic phase is dried over magnesium sulfate and evaporated under vacuum. The residue is filtered over silica gel with hexane/ethyl acetate mixtures, thus obtaining 2.20 g. of the above diol as a colorless oil.

IR: 3600, 3450 (broad), 2965, 2870, 978, 948 cm$^{-1}$.

12(c)

(1R,5S,6R,7R)-7-Hydroxy-6-[(E)-3α,β-hydroxy-3-methyloct-1-en-6-inyl]bicyclo[3,3,0]octan-3-one 2 g. of the diol prepared according to Example 12(b) is agitated for 20 hours with 50 ml. of a mixture of acetic acid/water/tetrahydrofuran (65/35/10). The mixture is evaporated under vacuum while adding toluene, the residue is taken up in methylene chloride and shaken in succession with sodium bicarbonate solution and brine, dried over magnesium sulfate, and evaporated under vacuum, thus obtaining 1.6 g. of the above ketone as an oil.

IR: 3600, 3450 (broad), 2965, 2860, 1738, 976 cm$^{-1}$.

12(d)

(1R,5S,6R,7R)-7-(Tetrahydropyran-2-yloxy)-6-[(E)-3α,β-methyl-3-(tetrahydropyran-2-yloxy)-oct-1-en-6-inyl]bicyclo[3,3,0]octan-3-one A mixture of 1 g. of the ketone prepared according to Example 12(c), 50 ml. of methylene chloride, 1.5 ml. of dihydropyran, and 10 mg. of p-toluenesulfonic acid is agitated for 30 minutes at 0°–5°. Then the mixture is diluted with methylene chloride, shaken with sodium bicarbonate solution and brine, dried over magnesium sulfate, and evaporated under vacuum. The residue is chromatographed on silica gel with hexane/ethyl acetate mixtures, thus obtaining 1.25 g. of the above bis(tetrahydropyranyl) ether as a colorless oil.

IR: 2960, 2865, 1738, 978 cm$^{-1}$.

EXAMPLE 13

5-{(E)-(1S,5S,6R,7R)-7-Hydroxy-6-[(E)-(4RS)-3α-hydroxy-4-methyloct-1-en-6-inyl]bicyclo[3,3,0]octan-3-ylidene}pentanoic Acid Methyl Ester A solution of 100 mg. of 5-{(E)-(1S,5S,6R,7R)-7-hydroxy-6-[(E)-(4RS)-3α-hydroxy-4-methyloct-1-en-6-inyl]bicyclo[3,3,0]octan-3-ylidene}-pentanoic acid (preparation see Example 11) in 5 ml. of methylene chloride is combined under agitation dropwise at 0° with an ethereal diazomethane solution until the mixture assumes a permanent yellow coloring. After evaporation of the solvent, the residue is purified by chromatography on silica gel with methylene chloride/1% isopropanol, thus obtaining 90 mg. of the title compound as an oil.

IR: 3600, 2960, 2865, 1735, 978 cm$^{-1}$.

EXAMPLE 14

5-{(E)-(1S,5S,6R,7R)-7-Hydroxy-6-[(E)-(4RS)-3α-hydroxy-4-methyloct-1-en-6-inyl]bicyclo[3,3,0]octan-3-ylidene}pentanoic Acid Tris (hydroxymethyl)aminomethane Salt At 65°, a solution of 121 mg. of tris(hydroxymethyl)aminomethane in 0.4 ml. of water is added to a solution of 360 mg. of 5-{(E)-(1S,5S,6R,7R)-7-hydroxy-6-[(E)-(4RS)-3α-hydroxy-4-methyloct-1-en-6-inyl]bicyclo[3,3,0]octan-3-ylidene}-pentanoic acid (preparation see Example 11) in 60 ml. of acetonitrile. The mixture is allowed to cool under agitation; after 16 hours, the product is decanted from the solvent, and the residue is dried at 25° and under 0.1 torr, thus obtaining 320 mg. of the title compound as a waxy mass.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a 3-oxo-7-hydroxy-bicyclo[3,3,0]octan-2-ylcarboxylic acid ester of the formula

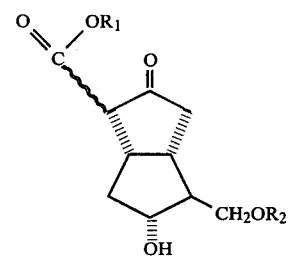

wherein $R_1$ is alkyl of 1–6 carbon atoms or phenalkyl of 7–10 carbon atoms and $R_2$ is hydrogen, alkyl of 1–6 carbon atoms, phenalkyl of 7–10 carbon atoms, tetrahydropyranyl, tetrahydrofuranyl, α-ethoxyethyl, tri-$C_{1-4}$-alkylsilyl wherein the alkyl moieties can optionally be substituted by phenyl, or

wherein $R_3$ is alkyl of 1–6 carbon atoms or aryl of 6–12 carbon atoms, comprising oxidizing the corresponding 7-hydroxy-2-oxabicyclo[3,3,0]octan-3-ylideneacetic acid ester of the formula

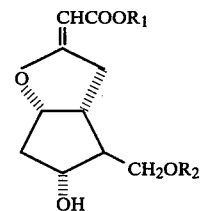

wherein $R_1$ and $R_2$ are as defined above, to form the corresponding ketone, reacting the latter with a base and then reducing to prepare the 3-oxo-7-hydroxy-bicyclo[3,3,0]octan-2-ylcarboxylic acid ester.

2. A process of claim 1 wherein the base is 1,5-diazabicyclo[4,3,0]non-5-ene or 1,8-diazabicyclo[5,4,0]undec-7-ene, potassium tert-butylate or sodium tert-butylate.

3. A process of claim 2 wherein the base is 1,5-diazabicyclo[4,3,0]non-5-ene or 1,8-diazabicyclo[5,4,0]undec-7-ene.

4. A process of claim 1 wherein the oxidation step is conducted by the Moffat-Pfitzner method or by oxidizing with an oxidizing agent which is Collins reagent, Jones reagent, pyridinium chlorochromate or pyridinium dichromate.

5. A process of claim 1 wherein the ketone prepared by the oxidation step is further reacted without any purification.

6. A process of claim 1 wherein the reaction with the base is conducted at −40° to +60° C.

7. A process of claim 6 wherein the reaction with the base is conducted in the presence of an inert solvent.

8. A process of claim 1 wherein the reduction step is effected by reducing with a reducing agent which is sodium borohydride, lithium tri-tert-butoxyaluminum hydride, zinc borohydride or aluminum isopropylate.

9. A process for preparing a compound of the formula

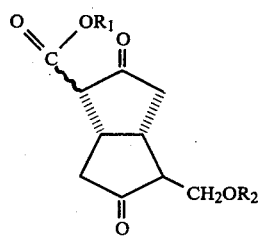

wherein
$R_1$ is alkyl of 1–6 carbon atoms or phenyalkyl of 7–10 carbon atoms and
$R_2$ is hydrogen, alkyl of 1–6 carbon atoms, phenalkyl of 7–10 carbon atoms, tetrahydropyranyl, tetrahydrofuranyl, α-ethoxyethyl, tri-$C_{1-4}$ alkylsilyl wherein the alkyl moieties can optionally be substituted by phenyl, or

wherein $R_3$ is alkyl of 1–6 carbon atoms or aryl of 6–12 carbon atoms, comprising reacting a corresponding compound of the formula

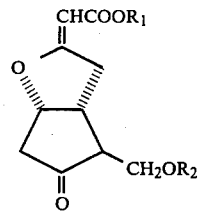

with a base.

* * * * *